(12) United States Patent
Kojima

(10) Patent No.: US 11,583,165 B2
(45) Date of Patent: Feb. 21, 2023

(54) MEDICAL SIGNAL PROCESSING DEVICE, CAP MEMBER, AND MEDICAL SIGNAL PROCESSING METHOD

(71) Applicant: Sony Olympus Medical Solutions Inc., Tokyo (JP)

(72) Inventor: Koji Kojima, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 17/134,538

(22) Filed: Dec. 28, 2020

(65) Prior Publication Data

US 2021/0251469 A1   Aug. 19, 2021

(30) Foreign Application Priority Data

Feb. 18, 2020 (JP) .............................. JP2020-025477

(51) Int. Cl.
| | |
|---|---|
| *A61B 1/005* | (2006.01) |
| *H04N 5/235* | (2006.01) |
| *A61B 1/00* | (2006.01) |
| *A61B 1/04* | (2006.01) |
| *A61B 1/06* | (2006.01) |
| *H04N 5/225* | (2006.01) |

(52) U.S. Cl.
CPC ...... *A61B 1/0005* (2013.01); *A61B 1/000095* (2022.02); *A61B 1/00137* (2013.01); *A61B 1/043* (2013.01); *A61B 1/0638* (2013.01); *A61B 1/0655* (2022.02); *H04N 5/2351* (2013.01); *H04N 5/2354* (2013.01); *A61B 1/00045* (2013.01); *A61B 1/00078* (2013.01); *A61B 1/00105* (2013.01); *A61B 1/00114* (2013.01); *A61B 1/00117* (2013.01); *A61B 1/042* (2013.01); *A61B 1/0669* (2013.01); *H04N 2005/2255* (2013.01)

(58) Field of Classification Search
None
See application file for complete search history.

(56) References Cited

U.S. PATENT DOCUMENTS

| | | | |
|---|---|---|---|
| 2017/0035280 A1* | 2/2017 | Yang | ..................... A61B 1/0669 |
| 2017/0251912 A1* | 9/2017 | Kato | ................... A61B 1/00009 |
| 2019/0110686 A1* | 4/2019 | Kato | ................... G01N 21/6456 |

FOREIGN PATENT DOCUMENTS

WO   WO-2018008062 A1 *   1/2018   ......... A61B 1/00009

* cited by examiner

*Primary Examiner* — Samuel D Fereja
(74) *Attorney, Agent, or Firm* — Xsensus LLP

(57) ABSTRACT

A medical signal processing device includes: an acquisition unit is configured to acquire a first image signal acquired by emission of first light onto an object, and a second image signal acquired by emission of second light onto the object, the first light being in a wavelength band including visible light, and the second light exciting a fluorescent substance included in the object; a detection unit configured to detect each of a signal level of the visible light included in the first image signal and a signal level of fluorescence included in the second image signal; and a calculation unit configured to calculate a correction coefficient to correct the signal level of the fluorescence by using a result of the detection by the detection unit.

3 Claims, 7 Drawing Sheets

MEDICAL SIGNAL PROCESSING DEVICE, CAP MEMBER, AND MEDICAL SIGNAL PROCESSING METHOD

CROSS-REFERENCE TO RELATED APPLICATION

This application claims priority from Japanese Application No. 2020-025477, filed on Feb. 18, 2020, the contents of which are incorporated by reference herein in its entirety.

BACKGROUND

The present disclosure relates to a medical signal processing device, a cap member, and a medical signal processing method.

In an endoscope, a technique of generating a synthetic image by synthesizing a white light image and a fluorescence image is known (see, for example, JP 2007-75198 A).

SUMMARY

When synthesizing a white light image and a fluorescence image, it is difficult to make a ratio of emission of white light to emission of excitation light of fluorescence constant. When this ratio changes, a variation is generated in brightness of the fluorescence image with respect to brightness of the white light image even when a fluorescence agent of the same concentration is added and observation is performed in the same environment.

According to one aspect pf the present disclosure, there is provided a medical signal processing device including: an acquisition unit is configured to acquire a first image signal acquired by emission of first light onto an object, and a second image signal acquired by emission of second light onto the object, the first light being in a wavelength band including visible light, and the second light exciting a fluorescent substance included in the object; a detection unit configured to detect each of a signal level of the visible light included in the first image signal and a signal level of fluorescence included in the second image signal; and a calculation unit configured to calculate a correction coefficient to correct the signal level of the fluorescence by using a result of the detection by the detection unit.

DETAILED DESCRIPTION

Figure 1:
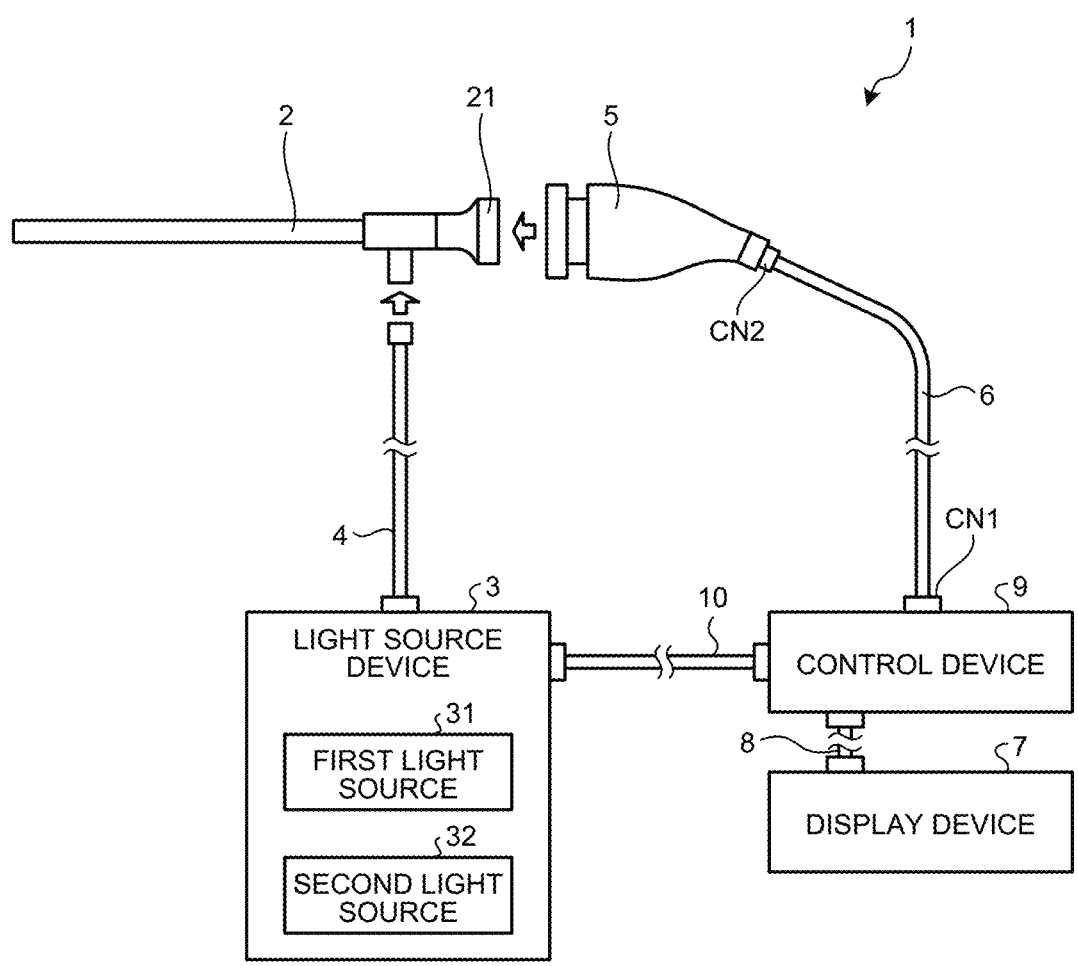
FIG. 1 is a view illustrating a configuration of a medical observation system.

In the following, modes for carrying out the present disclosure (hereinafter, referred to as "embodiment") will be described with reference to the accompanying drawings. Note that the present disclosure is not limited to the embodiment described in the following. Furthermore, the same reference sign is assigned to identical parts in the drawings.

FIG. 1 is a view illustrating a configuration of a medical observation system including a medical signal processing device according to an embodiment. A medical observation system 1 illustrated in the drawing is a system that is used in a medical field and that captures (observe) an inside of a living body to be an object (observation target). This medical observation system 1 includes an endoscope 2, a light source device 3, a light guide 4, a camera head 5, a first transmission cable 6, a display device 7, and a second transmission cable 8, a control device 9 that is a medical signal processing device according to the embodiment, and a third transmission cable 10.

The endoscope 2 has an elongated shape that is rigid as a whole, and is inserted into a living body. In this endoscope 2, an optical system that includes one or a plurality of lenses and that collects light from an object is provided. Note that the endoscope 2 may be a flexible endoscope having a rigid distal end portion.

One end of the light guide 4 is connected to the light source device 3, and light to irradiate an inside of a living body is supplied therefrom to the light guide 4 under the control of the control device 9. This light source device 3 includes a first light source 31 and a second light source 32.

The first light source 31 emits first light in a wavelength band including visible light. The first light source 31 includes, for example, three light emitting diodes (LED) of red, blue, and green, and emits white light as the first light. A luminance component is green (495 to 570 nm). Note that when correction coefficient calculation processing (described later) is executed, the first light source 31 may emit green light as the first light.

The second light source 32 emits second light having a wavelength band different from that of the first light. In the present embodiment, the second light source 32 includes, for example, a semiconductor laser, has a near-infrared wavelength band as the second light, and emits excitation light that excites a fluorescent substance such as indocyanine green (ICG). A central wavelength of the excitation light is around 774 nm, and a central wavelength of fluorescence by ICG is around 805 nm. A wavelength band of the excitation light and a wavelength band of the fluorescence may be set in such a manner as to partially overlap or may be set in such a manner as not to overlap at all.

In the light source device 3, the first light source 31 and the second light source 32 are alternately driven in a time division manner under the control of the control device 9. Note that the light source device 3 is configured separately from the control device 9 in the present embodiment. However, a light source device 3 may be configured integrally with a control device 9.

One end of the light guide 4 is detachably connected to the light source device 3, and the other end thereof is detachably connected to the endoscope 2. The light guide 4 propagates the light (white light or excitation light) supplied from the light source device 3 from the one end to the other end and supplies the light to the endoscope 2. In a case where white light is emitted to an object such as a living body, the white light reflected by the object is collected by the optical system in the endoscope 2. Also, in a case where excitation light is emitted to the object, the excitation light reflected by the object and fluorescence emitted by a fluorescent substance such as ICG included in the object are collected by the optical system in the endoscope 2.

The camera head 5 is detachably connected to an eyepiece 21 provided at a proximal end of the endoscope 2, and captures the light collected by the endoscope 2 and outputs a digital image signal acquired by the imaging (RAW signal) under the control of the control device 9. The detailed configuration of the camera head 5 will be described later.

One end of the first transmission cable 6 is detachably connected to the control device 9 via a connector CN1, and the other end thereof is detachably connected to the camera head 5 via a connector CN2. The first transmission cable 6 transmits the image signal and the like output from the camera head 5 to the control device 9, and also transmits a control signal, synchronization signal, clock, electric power, and the like output from the control device 9 to the camera head 5. Note that the image signal and the like from the camera head 5 to the control device 9 through the first transmission cable 6 may be transmitted as an optical signal or an electric signal. The same applies to transmission of the control signal, synchronization signal, and clock from the control device 9 to the camera head 5 through the first transmission cable 6.

The display device 7 includes a display, in which liquid crystal, organic electro luminescence (EL), or the like is used, and displays an image based on a video signal from the control device 9 under the control of the control device 9.

One end of the second transmission cable 8 is detachably connected to the display device 7, and the other end thereof is detachably connected to the control device 9. Then, the second transmission cable 8 transmits the video signal output by the control device 9 to the display device 7.

The control device 9 includes a central processing unit (CPU), a field-programmable gate array (FPGA), or the like, and comprehensively controls operations of the light source device 3, the camera head 5, and the display device 7. The detailed configuration of the control device 9 will be described later.

One end of the third transmission cable 10 is detachably connected to the light source device 3, and the other end thereof is detachably connected to the control device 9. Then, the third transmission cable 10 transmits the control signal from the control device 9 to the light source device 3.

Figure 2:
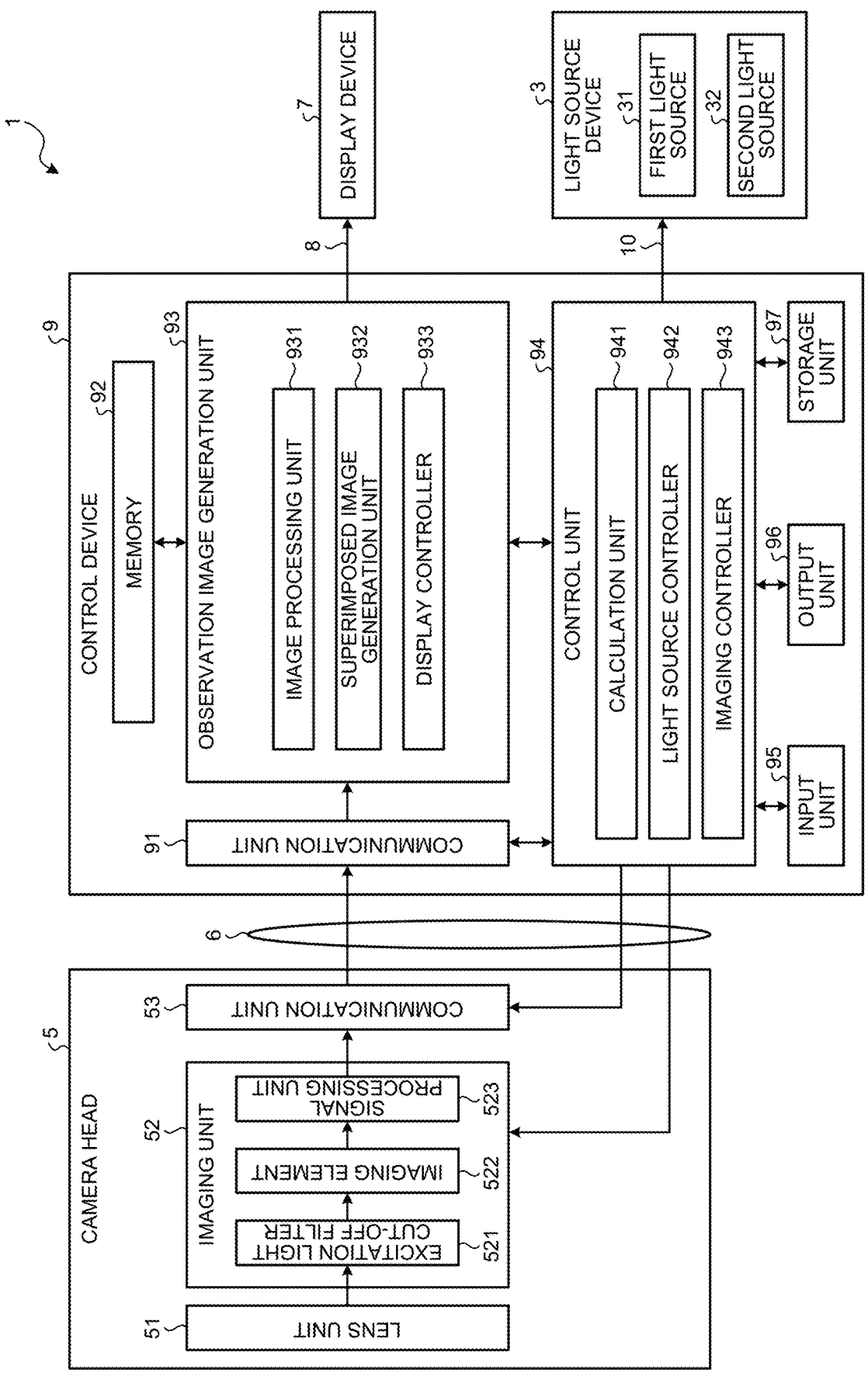
FIG. 2 is a block diagram illustrating configurations of a camera head and a control device.

FIG. 2 is a block diagram illustrating the configurations of the camera head 5 and the control device 9.

First, the configuration of the camera head 5 will be described. The camera head 5 includes a lens unit 51, an imaging unit 52, and a communication unit 53.

The lens unit 51 includes one or a plurality of lenses, and forms an image of the light (white light, excitation light, and fluorescence) collected by the endoscope 2 on an imaging surface of an imaging element included in the imaging unit 52.

The imaging unit 52 captures the inside of the living body under the control of the control device 9. The imaging unit 52 includes an excitation light cut-off filter 521, an imaging element 522, and a signal processing unit 523.

The excitation light cut-off filter 521 is provided between the lens unit 51 and the imaging element 522, and transmits white light and fluorescence while removing excitation light. The excitation light cut-off filter 521 includes, for example, a band-stop filter.

The imaging element 522 includes a charge coupled device (CCD), a complementary metal oxide semiconductor (CMOS), or the like that receives light transmitted through the excitation light cut-off filter 521 and that performs conversion thereof into an electric signal (analog signal). The signal processing unit 523 generates and outputs a digital image signal (RAW signal) by performing signal processing on the electric signal generated in the imaging element 522.

The communication unit 53 functions as a transmitter that transmits the RAW signal output from the imaging unit 52 to the control device 9 through the first transmission cable 6. This communication unit 53 includes, for example, a high-speed serial interface that communicates with the control device 9 through the first transmission cable 6 at a transmission rate equal to or higher than 1 Gbps.

Next, the configuration of the control device 9 will be described.

The control device 9 includes a communication unit 91, a memory 92, an observation image generation unit 93, a control unit 94, an input unit 95, an output unit 96, and a storage unit 97. The control device 9 may be alternatively set to a normal observation mode, and a calibration mode of calculating a correction coefficient to correct a signal level of fluorescence.

Through the first transmission cable 6, the communication unit 91 receives the RAW signal output from the communication unit 53 of the camera head 5. The communication unit 91 functions as an acquisition unit that acquires a first image signal acquired by emission of the first light to the object, and a second image signal acquired by emission of the second light to the object. The communication unit 91 includes, for example, a high-speed serial interface that communicates with the communication unit 53 at a transmission rate equal to or higher than 1 Gbps.

The memory 92 includes, for example, a dynamic random access memory (DRAM) or the like. The memory 92 temporarily stores a plurality of frames of RAW signals acquired by the communication unit 91.

The observation image generation unit 93 generates a signal of an observation image by using a RAW signal under the control of the control unit 94. The observation image generation unit 93 includes an image processing unit 931, a superimposed image generation unit 932, and a display controller 933.

The image processing unit 931 functions as a detection unit that detects a signal level by using a RAW signal. Also, after performing various kinds of image processing such as white balance adjustment processing, demosaicing processing, and gamma correction processing, the image processing unit 931 converts signal values of R, G, and B into signal values of Y, Cb, and Cr (luminance/color-difference signal value) by a predetermined calculation. In a case where the control device 9 is in the observation mode, the image processing unit 931 corrects a signal level of fluorescence according to a correction coefficient that is calculated by a calculation unit 941 (described later) in the calibration mode and that is stored in the memory 92.

The superimposed image generation unit 932 generates a signal of a superimposed image by superimposing a white light image and fluorescence image on which the image processing is performed in the image processing unit 931.

The display controller 933 generates a video signal for a display from an image signal acquired from the image processing unit 931 or the superimposed image generation unit 932, and outputs the generated video signal to the display device 7 through the second transmission cable 8.

The control unit 94 includes a calculation unit 941, a light source controller 942, and an imaging controller 943.

The calculation unit 941 calculates a correction coefficient to correct a signal level of fluorescence by using a signal level of a luminance component (green) of a RAW signal detected by the image processing unit 931 in emission of white light, and a signal level of fluorescence of a RAW signal detected thereby in emission of excitation light. More specifically, the calculation unit 941 calculates a correction coefficient $\alpha=<G>/\alpha_0<FS>$ by using an average signal level $<G>$ of the luminance component in a detection period of a predetermined length and an average signal level $<FS>$ of the fluorescence in the detection period of the same length. Here, $\alpha_0$ on the right side is a target correction coefficient (target value of a correction coefficient) determined on the basis of a previously-set ratio. This target correction coefficient $\alpha_0$ may be set according to a type of an endoscope or the like, or may be set manually from the input unit 95 by a user such as a doctor. The calculation unit 941 writes and stores the calculated correction coefficient $\alpha$ into the storage unit 97.

The input unit 95 includes an operation device such as a mouse, a keyboard, and a touch panel, and receives an operation input by the user. Then, the input unit 95 outputs a signal corresponding to the operation input to the control unit 94.

The output unit 96 includes a display unit such as liquid crystal or organic EL, a lamp, a speaker, and the like, and outputs various kinds of information including information related to an operation of the control device 9.

The storage unit 97 stores a correction coefficient used in the observation mode, a program executed by the control unit 94, information necessary for processing by the control unit 94, and the like. The storage unit 97 includes a RAM, a read only memory (ROM), or the like.

Figure 3:
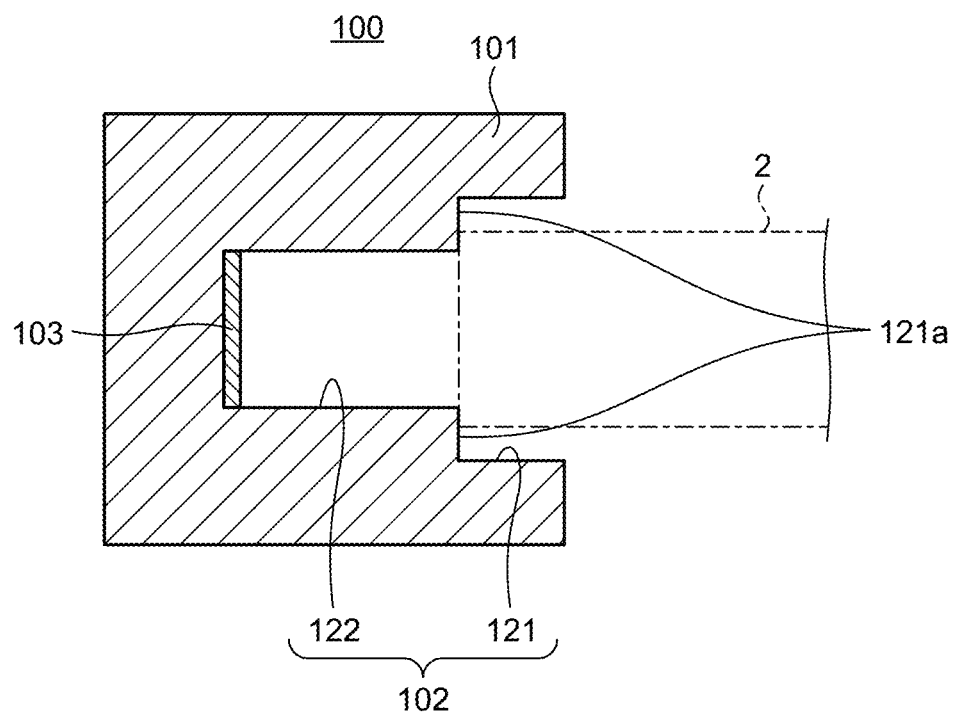
FIG. 3 is a cross-sectional view schematically illustrating a configuration of a cap member according to an embodiment.

FIG. 3 is a cross-sectional view schematically illustrating a configuration of a cap member according to the embodiment. The cap member 100 illustrated in the drawing is used by being attached to a distal end portion of the endoscope 2 when the correction coefficient calculation processing is performed in the medical observation system 1. In FIG. 3, the endoscope 2 attached to the cap member 100 is illustrated by a dashed line.

The cap member 100 includes a bottomed hollow tubular main body 101 in which one bottom surface is opened, and a chart portion 103 provided on a bottom surface of a hollow portion 102 of the main body 101.

The hollow portion 102 has a stepped shape having a large diameter portion 121 capable of housing the distal end portion of the endoscope 2, and a small diameter portion 122 which has a smaller diameter than the large diameter portion 121 and to a bottom surface of which the chart portion 103 is attached. An end portion 121a at a boundary between the large diameter portion 121 and the small diameter portion 122 forms an annular shape parallel to a width direction (vertical direction in FIG. 3) orthogonal to ta depth direction (horizontal direction in FIG. 3) of the hollow portion 102. The end portion 121a has a function of abutting the distal end of the endoscope 2 and performing positioning when the cap member 100 is attached to the distal end portion of the endoscope 2. A width in a radial direction of an annulus of the end portion 121a is set in such a manner that distal ends of a plurality of endoscopes 2 having different diameters may abut.

The chart portion 103 has one or a plurality of quantum dots that reflects excitation light and emits fluorescence corresponding to the excitation light when irradiated with the excitation light. In a case of being irradiated with white light, the chart portion 103 reflects the white light. Also, in a case where the chart portion 103 is irradiated with light of a luminance component (green light), the light is reflected.

Note that the chart portion 103 may have a fluorescent resin including a fluorescent substance such as ICG instead of the quantum dots.

Since it is assumed that the cap member 100 is a disposable type, a fluorescent substance such as ICG may be provided on a surface of the chart portion 103 and emit fluorescence. In a case where a fluorescent substance is provided on the chart portion 103, the cap member 100 is stored in a light-blocking state.

Figure 4:
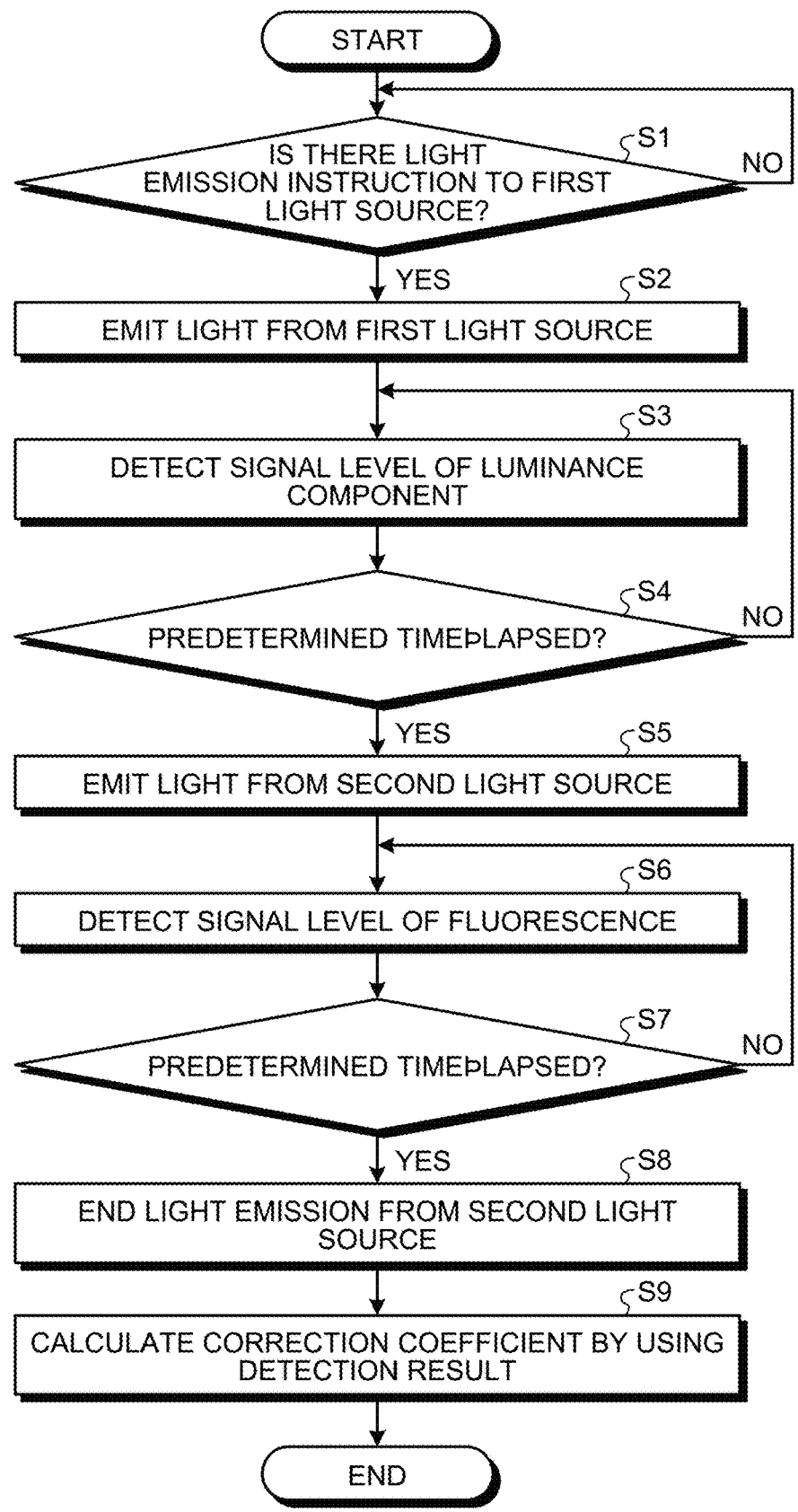
FIG. 4 is a flowchart illustrating an outline of a correction coefficient calculation processing performed by a medical signal processing device according to the embodiment.

FIG. 4 is a flowchart illustrating an outline of the correction coefficient calculation processing performed in a case where the control device 9 is set to the calibration mode. It is assumed that the imaging unit 52 of the camera head 5 constantly operates and outputs a RAW signal to the control device 9 during the processing described in the following. Also, in the processing described below, it is assumed that the cap member 100 is attached to the distal end portion of the endoscope 2 at least while the first light source 31 or the second light source 32 emits light.

First, when the input unit 95 receives an input of a light emission instruction to the first light source 31 (Step S1: Yes), the light source controller 942 causes the first light source 31 to emit light (Step S2). At this time, the light source controller 942 may cause the first light source 31 to emit white light or to emit only green light that is a luminance component. In a case where the input unit 95 does not receive the input of the light emission instruction to the first light source 31 in Step S1 (Step S1: No), the control device 9 repeats Step S1.

Subsequently, the image processing unit 931 detects a signal level of a luminance component of a RAW signal (first image signal) acquired from the camera head 5 (Step S3). The image processing unit 931 writes and stores the detected signal level into the storage unit 97 together with time information.

Then, in a case where a predetermined time elapses after the image processing unit 931 starts detecting the signal level (Step S4: Yes), the light source controller 942 ends the light emission of the first light source 31 and causes the second light source 32 to emit light (Step S5). On the one hand, in a case where the predetermined time does not elapse after the image processing unit 931 starts the detection (Step S4: No), the control device 9 returns to Step S3.

Subsequently, the image processing unit 931 detects a signal level of a RAW signal of fluorescence (second image signal) acquired from the camera head 5 (Step S6). The image processing unit 931 writes and stores the detected signal level into the storage unit 97 together with time information.

Then, in a case where a predetermined time elapses after the image processing unit 931 starts the detection (Step S7: Yes), the light source controller 942 ends the light emission of the second light source 32 (Step S8). On the one hand, in a case where the predetermined time does not elapse after the image processing unit 931 starts the detection (Step S7: No), the control device 9 returns to Step S6.

After Step S8, the calculation unit 941 reads results of the detection in Step S3 and Step S6 from the storage unit 97 and calculates a correction coefficient $\alpha$ of a signal level of a fluorescence signal (Step S9). At this time, the calculation unit 941 first calculates each of an average signal level $<G>$ of a luminance component and an average signal level $<FS>$ of fluorescence, and calculates the correction coefficient $\alpha=<G>/\alpha_0<FS>$ by using results of the calculation. Then, the control device 9 ends the series of processing.

Note that light emission order of the first light source 31 and the second light source 32 may be reversed, and the input unit 95 may receive an input of a light emission instruction to the second light source 32. Also, a predetermined time in Step S5 and that in Step S7 may be the same or different. Also, the input unit 95 may receive an on/off instruction to each of the first light source 31 and the second light source 32.

The above processing is performed before the endoscope 2 is attached to the camera head 5 and examination is performed. As a result, even in a case where a different type of endoscope 2 is used for each time of examination, a correction coefficient α suitable for the endoscope 2 may be set. Note that the above processing may be performed at the time of shipment.

According to the present embodiment described above, a correction coefficient to correct a signal level of fluorescence is calculated by utilization of a signal level of a luminance component and a signal level of fluorescence which levels are detected from image signals acquired individually. Thus, it is possible to adjust a variation generated due to an endoscope, a light source device, a light guide, a camera head, and other factors, and to control a variation in brightness of a fluorescence image with respect to brightness of a white light image. As a result, when a phosphor having a certain concentration is observed, the observation may be performed with the same brightness constantly and fluorescence may be quantified. Also, according to the present embodiment, a cap member including a bottomed hollow tubular main body in which one bottom surface is opened and a distal end portion of an endoscope is inserted into a hollow portion, and a chart portion that is included on a bottom surface of the hollow portion, reflects first light, reflects second light, and emits fluorescence excited by the second light is used. Thus, it is possible to make imaging conditions of when the first and second light is emitted the same, and to accurately control a variation in brightness of a fluorescence image with respect to brightness of a white light image.

Figure 5:
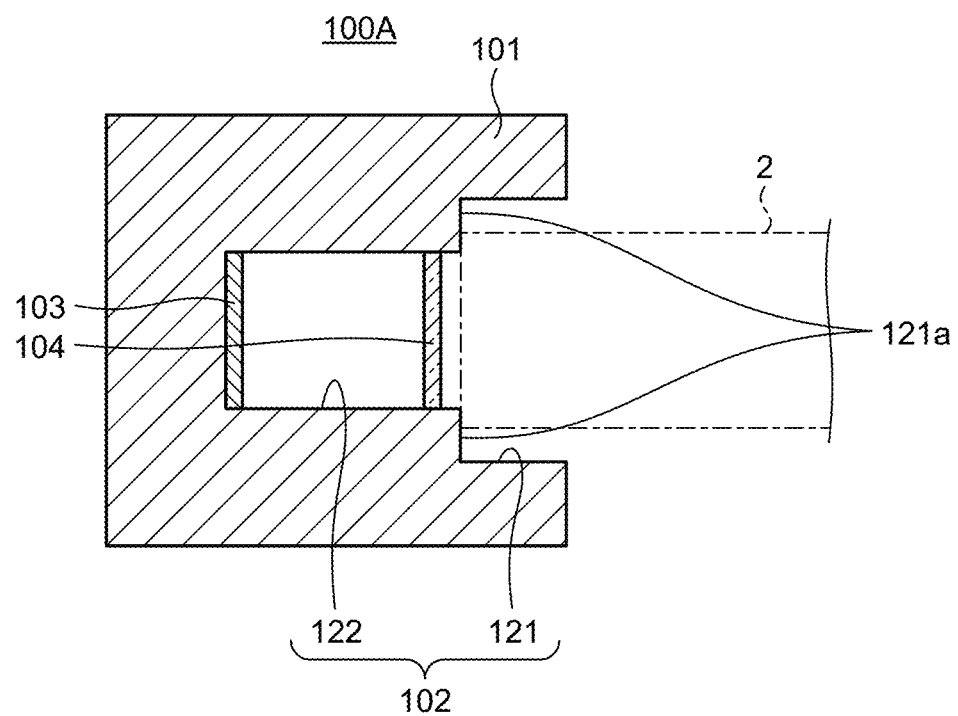
FIG. 5 is a cross-sectional view schematically illustrating another configuration of a cap member.

Although modes for carrying out the present disclosure have been described in the above, the above-described embodiment is not a limitation. FIG. 5 is a cross-sectional view schematically illustrating another configuration of a cap member. In addition to the configuration of the cap member 100 described above (see FIG. 3), a cap member 100A illustrated in the drawing further includes a cover member 104 that is provided in a small diameter portion 122 and that transmits first light, second light, and fluorescence. The cover member 104 is made, for example, of sapphire glass having resistance to heat and chemicals, is soldered to a main body 101 near a boundary with a large diameter portion 121, and airtightly closes a region including a chart portion 103. As a result, the cap member 100A may be sterilized by an autoclave, and the cap member 100A may be used repeatedly. Note that the chart portion 103 in this case includes a quantum dot, a fluorescent resin, or the like instead of a fluorescent substance.

Also, the present disclosure is not limited to a configuration in which white light and excitation light are emitted in a time-divided manner and observation is performed. For example, a configuration in which white light and excitation light are simultaneously emitted and observation is performed may be also applied.

Figure 6:
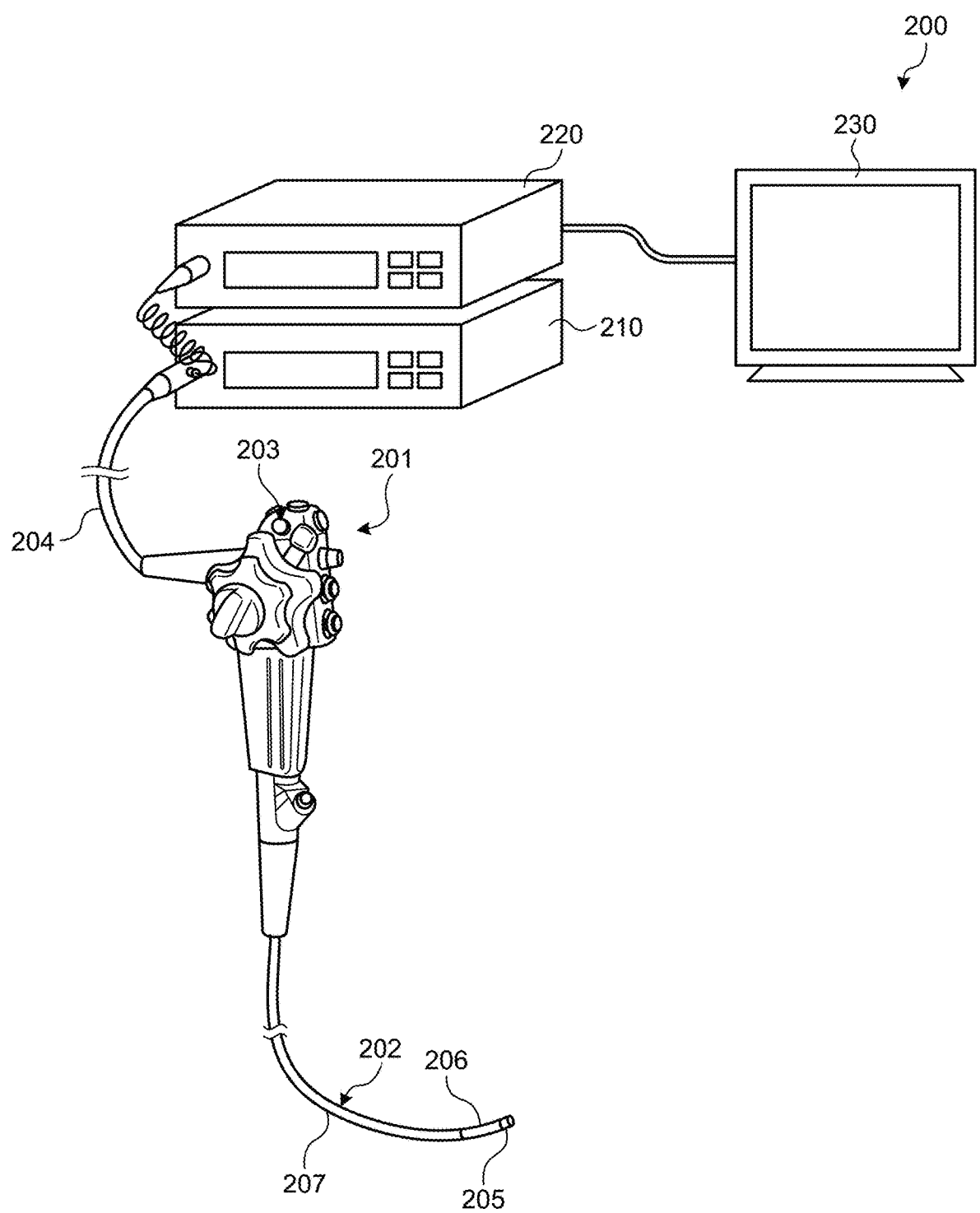
FIG. 6 is a view illustrating a second configuration example of a medical observation system.

FIG. 6 is a view illustrating a second configuration example in a medical observation system. A medical observation system 200 illustrated in the drawing is an endoscopic system. The medical observation system 200 includes an endoscope 201 that captures an in-vivo image of an observed region and generates an imaging signal by insertion of an insertion portion 202 into an object, a light source device 210 that generates first light and second light emitted from the endoscope 201 to the object, a control device 220 that performs predetermined image processing on the imaging signal acquired by the endoscope 201 and comprehensively controls an operation of the entire medical observation system 200, and a display device 230 that displays an in-vivo image on which the image processing is performed by the control device 220. The control device 220 has a functional configuration similar to that of the control device 9. Also, in the medical observation system 200, correction coefficient calculation processing similar to that in the above-described embodiment is performed by utilization of a cap member that may be attached to a rigid distal end portion of the insertion portion 202.

The light source device 210 includes a first light source 31 and a second light source 32. The light source device 210 supplies the first light and the second light to the endoscope 201 under the control of the control device 220.

Figure 7:
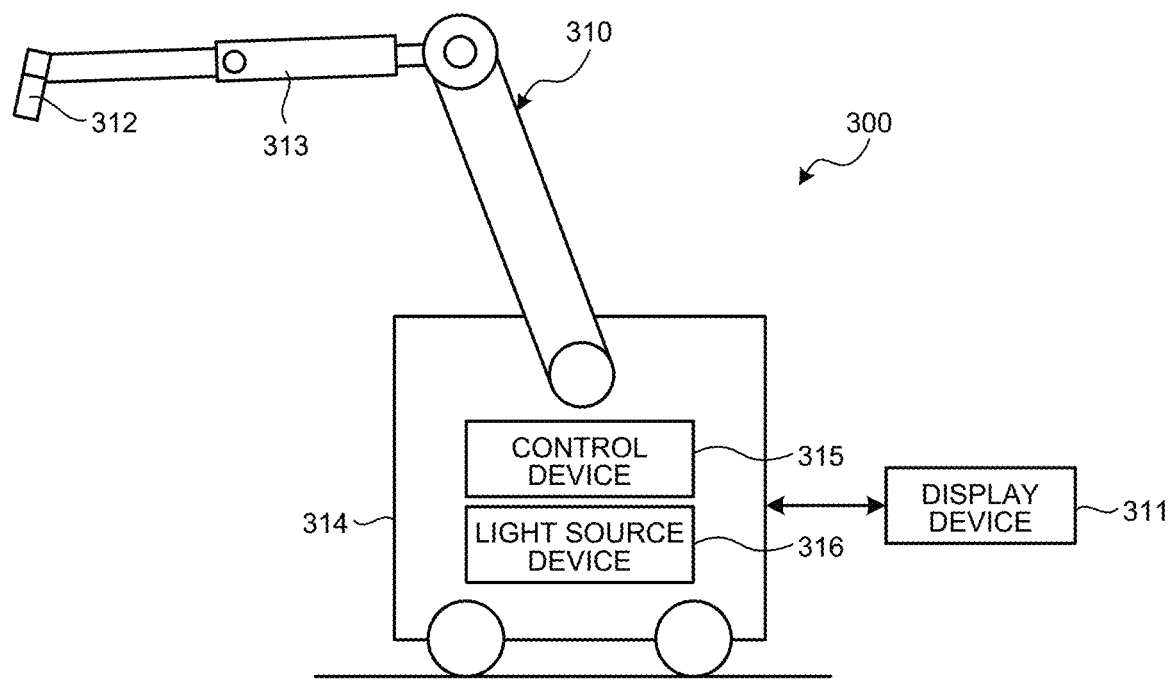
FIG. 7 is a view illustrating a third configuration example of a medical observation system.

FIG. 7 is a view illustrating a third configuration example of a medical observation system. A medical observation system 300 illustrated in the drawing is an operating microscope system. The medical observation system 300 includes a microscope device 310 that is a medical imaging device to perform imaging and to acquire an image to observe an object, and a display device 311 that displays the image captured by the microscope device 310. Note that a display device 311 and a microscope device 310 may be also configured integrally.

The microscope device 310 includes a microscope unit 312 that magnifies and captures a minute region of an object, a supporting portion 313 including an arm that is connected to a proximal end portion of the microscope unit 312 and rotatably supports the microscope unit 312, and a base unit 314 that rotatably holds a proximal end portion of the supporting portion 313 and that is movable on a floor surface. The base unit 314 includes a control device 315 that comprehensively controls an operation of the medical observation system 300, and a light source device 316 that generates first light and second light emitted from the microscope device 310 to the object. The control device 315 has a functional configuration similar to that of the control device 9. The light source device 316 includes a first light source 31 and a second light source 32. The light source device 316 supplies the first light and the second light to the microscope device 310 under the control of the control device 315. Note that the base unit 314 may be configured to support the supporting portion 313 by being fixed to a ceiling, wall surface, or the like instead of being provided movably on the floor surface.

The microscope unit 312 has, for example, a columnar shape and has the above-described lens unit 51 and imaging unit 52 inside. A switch that receives an input of an operation instruction to the microscope device 310 is provided on a side surface of the microscope unit 312. Cover glass that protects the inside is provided on an aperture plane at a lower end portion of the microscope unit 312 (not illustrated).

In the medical observation system 300 configured in such a manner, a user such as an operator may move the microscope unit 312, perform a zoom operation, or switch illumination light while operating various switches in a state of holding the microscope unit 312. In this case, by utilization of a cap member that may be attached to a distal end of the microscope unit 312, correction coefficient calculation processing is performed in a manner similar to that in the above-described embodiment. Note that a shape of the microscope unit 312 is preferably a shape elongated in an observation direction in such a manner that the user may easily hold the microscope unit 312 and change a viewing direction. Thus, the shape of the microscope unit 312 may be a shape other than the columnar shape, and may be a polygonal pillar shape, for example.

In the medical observation systems 200 and 300 described above, effects similar to those in the above-described embodiment may be acquired.

Note that the present technique may also have the following configurations.

(1) A medical signal processing device including:

an acquisition unit is configured to acquire a first image signal acquired by emission of first light onto an object, and a second image signal acquired by emission of second light onto the object, the first light being in a wavelength band including visible light, and the second light exciting a fluorescent substance included in the object;

a detection unit configured to detect each of a signal level of the visible light included in the first image signal and a signal level of fluorescence included in the second image signal; and a calculation unit configured to calculate a correction coefficient to correct the signal level of the fluorescence by using a result of the detection by the detection unit.

(2) The medical signal processing device according to (1), wherein the correction coefficient is a coefficient to set a ratio of the signal level of the visible light to the signal level of the fluorescence to a previously-set ratio.

(3) The medical signal processing device according to (2), wherein the calculation unit is configured to:

calculate each of a time average signal level of the visible light and a time average signal level of the fluorescence, and calculate the correction coefficient by using the time average signal level of the visible light, the time average signal level of the fluorescence, and a target correction coefficient determined on the basis of the previously-set ratio.

(4) The medical signal processing device according to any one of (1) to (3), wherein the first and second image signals are image signals captured by an endoscope, and the object reflects the first light when irradiated with the first light, and reflects the second light and emits fluorescence corresponding to the second light when irradiated with the second light.

(5) A cap member including:

a bottomed hollow tubular main body in which one bottom surface is opened and in which a distal end portion of an endoscope is inserted into a hollow portion; and a chart portion provided on a bottom surface of the hollow portion, wherein the chart portion reflects first light in a wavelength band including visible light when irradiated with the first light, reflects second light in a wavelength band different from that of the first light when irradiated with the second light, and has a fluorescent substance excited by the second light.

(6) The cap member according to (5), further including a cover member configured to airtightly close a part of the chart portion and the hollow portion and transmit the first light, the second light, and fluorescence emitted by the fluorescent substance.

(7) A medical signal processing method including:

(a) acquiring a first image signal acquired by emission of first light onto an object, the first light being in a wavelength band including visible light;

(b) detecting a signal level of the visible light included in the first image signal;

(c) acquiring a second image signal acquired by emission of second light onto the object, the second light exciting a fluorescent substance included in the object;

(d) detecting a signal level of fluorescence included in the second image signal; and (e) calculating a correction coefficient to correct the signal level of the fluorescence by using results of the detection in (b) and (d), wherein first processing from (a) to (b) and second processing from (c) to (d) are performed in arbitrary order.

According to the present disclosure, it is possible to control a variation in brightness of a fluorescence image with respect to brightness of a white light image.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical signal processing device comprising:

acquisition circuitry configured to acquire a first image signal acquired by emission of first light onto an object, and a second image signal acquired by emission of second light onto the object, the first light being in a wavelength band including visible light, and the second light exciting a fluorescent substance included in the object;

detection circuitry configured to detect each of a first signal level of the visible light included in the first image signal over a first detection period and a second signal level of fluorescence included in the second image signal over a second detection period having a same length as the first detection period, the first image signal and the second image signal being acquired individually; and calculation circuitry configured to calculate a correction coefficient to correct the signal level of the fluorescence in accordance with the first signal level and the second signal level detected by the detection circuitry, wherein the correction coefficient is a coefficient to set a ratio of the first signal level of the visible light to the second signal level of the fluorescence to a previously-set ratio, and the calculation circuitry is configured to:

calculate each of a time average signal level of the visible light and a time average signal level of the fluorescence, and calculate the correction coefficient by using the time average signal level of the visible light as the first signal level, the time average signal level of the fluorescence as the second signal level, and a target correction coefficient determined on the basis of the previously-set ratio.

2. The medical signal processing device according to claim 1, wherein the first and second image signals are image signals captured by an endoscope, and the object reflects the first light when irradiated with the first light, and reflects the second light and emits fluorescence corresponding to the second light when irradiated with the second light.

3. A medical signal processing method comprising:
(a) acquiring a first image signal acquired by emission of first light onto an object, the first light being in a wavelength band including visible light;
(b) detecting a first signal level of the visible light included in the first image signal over a first detection period;
(c) acquiring a second image signal acquired by emission of second light onto the object, the second light exciting a fluorescent substance included in the object;
(d) detecting a second signal level of fluorescence included in the second image signal over a second detection period having a same length as the first detection period, the first image signal and the second image signal being acquired individually; and
(e) calculating a correction coefficient to correct the signal level of the fluorescence, in accordance with the first signal level and the second signal level detected, wherein first processing from (a) to (h) and second processing from (c) to (d) are performed in arbitrary order, wherein the correction coefficient is a coefficient to set a ratio of the first signal level of the visible light to the second signal level of the fluorescence to a previously-set ratio; and calculating each of a time average signal level of the visible light and a time average signal level of the fluorescence, and calculating the correction coefficient by using the time average signal level of the visible light as the first signal level, the time average signal level of the fluorescence as the second signal level, and a target correction coefficient determined on the basis of the previously-set ratio.

* * * * *